(12) United States Patent
Liao et al.

(10) Patent No.: US 11,490,828 B2
(45) Date of Patent: Nov. 8, 2022

(54) BIOELECTRICAL IMPEDANCE MEASUREMENT DEVICE AND METHOD THEREOF

(71) Applicant: GOLDENSUNDA TECHNOLOGY CO., LTD., New Taipei (TW)

(72) Inventors: Chi-Yao Liao, New Taipei (TW); Chun-Feng Huang, New Taipei (TW)

(73) Assignee: GOLDENSUNDA TECHNOLOGY CO., LTD., New Taipei (TW)

( * ) Notice: Subject to any disclaimer, the term of this patent is extended or adjusted under 35 U.S.C. 154(b) by 303 days.

(21) Appl. No.: 16/835,316

(22) Filed: Mar. 31, 2020

(65) Prior Publication Data

US 2021/0186358 A1 Jun. 24, 2021

(30) Foreign Application Priority Data

Dec. 20, 2019 (TW) .................................. 108147009

(51) Int. Cl.
*A61B 5/053* (2021.01)
*A61B 5/0531* (2021.01)
*A61B 5/00* (2006.01)

(52) U.S. Cl.
CPC .......... *A61B 5/0531* (2013.01); *A61B 5/6825* (2013.01); *A61B 5/6829* (2013.01); *A61B 5/6838* (2013.01); *A61B 5/742* (2013.01); *A61B 2560/0266* (2013.01); *A61B 2562/04* (2013.01)

(58) Field of Classification Search
CPC ... A61B 5/0531; A61B 5/0537; A61B 5/6829; A61B 5/6825; A61B 5/6838; A61B 5/742
See application file for complete search history.

(56) References Cited

U.S. PATENT DOCUMENTS

| 2009/0171234 A1* | 7/2009 | Gurewitsch | A61B 5/053 600/547 |
| 2009/0216140 A1* | 8/2009 | Skrabal | A61B 5/4869 600/547 |
| 2013/0204098 A1* | 8/2013 | Chamney | A61B 5/0537 600/547 |
| 2013/0345592 A1* | 12/2013 | Leuner | A61B 5/0537 600/547 |
| 2014/0243699 A1* | 8/2014 | Wabel | A61B 5/0537 600/547 |

(Continued)

*Primary Examiner* — Eric F Winakur
(74) *Attorney, Agent, or Firm* — Leong C. Lei

(57) ABSTRACT

The bioelectrical impedance measurement device mainly includes a portable casing, a control member inside the portable casing, and an electrode assembly joined to the portable casing and electrically connected to the control member. The control member includes current generation element, a current collection and processing element, and a current protection element. The electrode assembly includes a left-hand contact and a right-hand contact, both configured on the portable casing. The electrode assembly further includes a left-foot contact, and a right-foot contact, both extended from the portable casing. The left-hand contact, right-hand contact, left-foot contact, and right-foot contact are respectively connected to a user's left hand, right hand, left foot, and right foot. The current generation element generates an electrical current, which enters the user's body through the limbs and then collected to calculate various bioelectrical impedances and to determine a required biological information.

7 Claims, 13 Drawing Sheets

(56) References Cited

U.S. PATENT DOCUMENTS

| | | | |
|---|---|---|---|
| 2015/0042360 A1* | 2/2015 | Graner | A61B 5/0537 |
| | | | 324/630 |
| 2016/0278707 A1* | 9/2016 | Rhein | A61B 5/6829 |
| 2017/0071500 A1* | 3/2017 | Von Maydell | A61B 5/0537 |

* cited by examiner

|  | 1k | 5k | 50k | 250k | 500k |
|---|---|---|---|---|---|
| A D  Impedance | Z1 | Z2 | Z3 | Z4 | Z5 |
| A B  Impedance | Y1 | Y2 | Y3 | Y4 | Y5 |
| A C  Impedance | X1 | X2 | X3 | X4 | X5 |
| B C  Impedance | W1 | W2 | W3 | W4 | W5 |
| B D  Impedance | V1 | V2 | V3 | V4 | V5 |
| C D  Impedance | U1 | U2 | U3 | U4 | U5 |

FIG. 13

BIOELECTRICAL IMPEDANCE MEASUREMENT DEVICE AND METHOD THEREOF

BACKGROUND OF THE INVENTION (a) Technical Field of the Invention

The present invention is generally related to bioelectrical impedance, and more particular to a device for measuring bioelectrical impedance and a related method.

(b) Description of the Prior Art

The body fat percentage (BFP) is a measure of fitness level, and it directly calculates a user's relative body composition without regard to height or weight. The different BFPs of two users of same heights and weights indicate their relative fitness levels and health conditions. A user may appear fit but the BFP may reveal his/her true health condition.

There are various methods in measuring BFP. Bioelectrical impedance analysis is a lower-cost approach, but its accuracy is often questionable.

SUMMARY OF THE INVENTION

The present invention therefore teaches a bioelectrical impedance measurement device that is easy to carry and also provides a more accurate result. The present invention also discloses a related method based on the bioelectrical impedance measurement device.

A major objective of the present invention is that the bioelectrical impedance measurement device includes an electrode assembly for respectively connecting a user's arms and legs so as to enhance its measurement accuracy.

The bioelectrical impedance measurement device mainly includes a portable casing, a control member inside the portable casing, and an electrode assembly joined to the portable casing and electrically connected to the control member. The control member includes current generation element, a current collection and processing element, and a current protection element. The electrode assembly includes a left-hand contact and a right-hand contact, both configured on the portable casing. The electrode assembly further includes a left-foot contact, and a right-foot contact, both extended from the portable casing.

To operate the bioelectrical impedance measurement device, the left-hand contact, right-hand contact, left-foot contact, and right-foot contact are respectively connected to the user's left hand, right hand, left foot, and right foot. The control member's current generation element generates an electrical current, which is limited by the current protection element to prevent harmful influence to the user. The electrical current then enters the user's body through the limbs and the electrical current is then collected through the limbs after it runs throughout the user's body. The electrode assembly directs the electrical current to the current collection and processing element, where various bioelectrical impedances are calculated and a required biological information is determined.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

BRIEF DESCRIPTION OF THE DRAWINGS

FIG. 13 shows the biological impedances obtained from the bioelectrical impedance measurement method of FIG. 12.

DETAILED DESCRIPTION OF THE PREFERRED EMBODIMENTS

Figure 1:
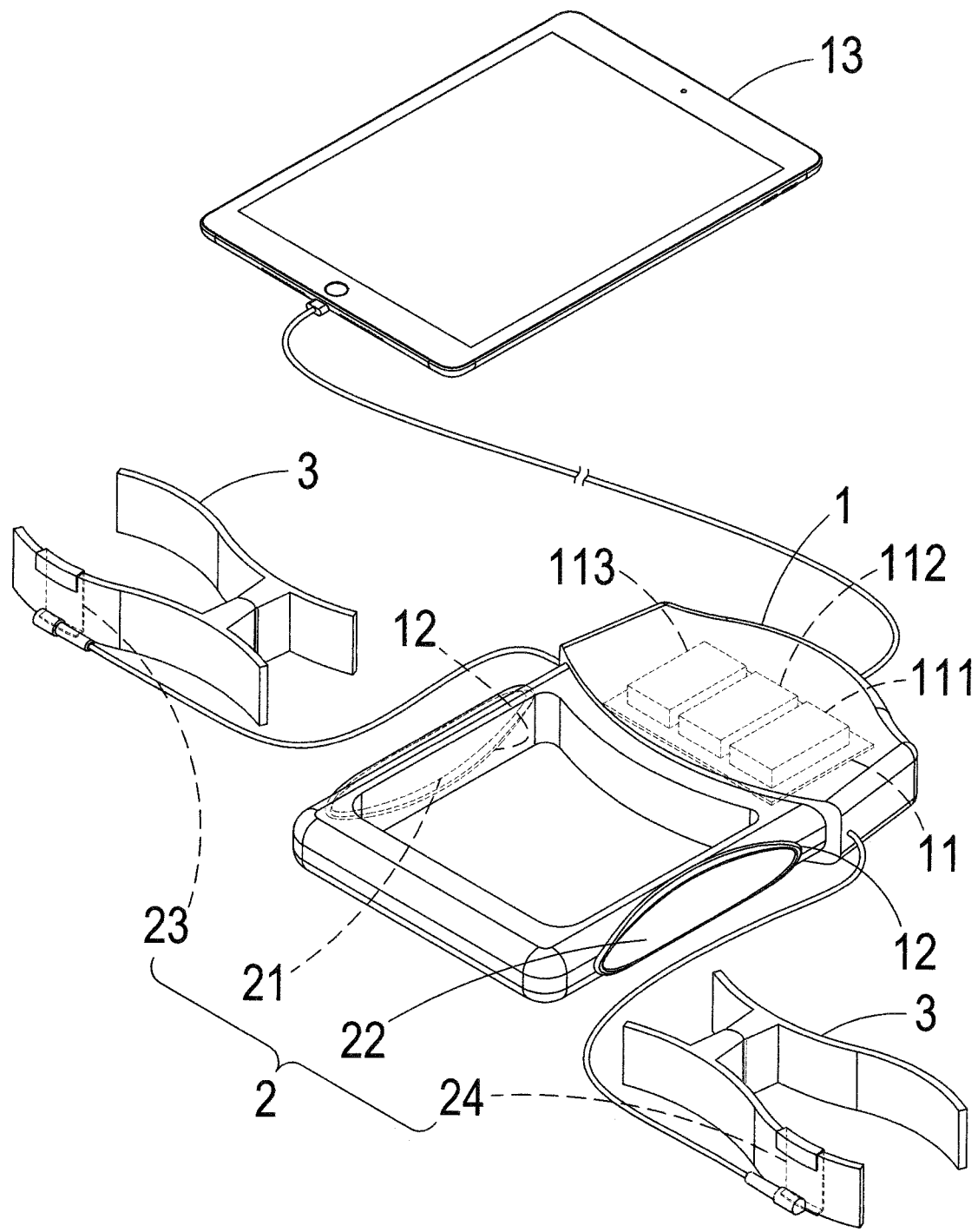
FIG. 1 is a perspective diagram showing a bioelectrical impedance measurement device according to a first embodiment of the present invention.
Figure 2:
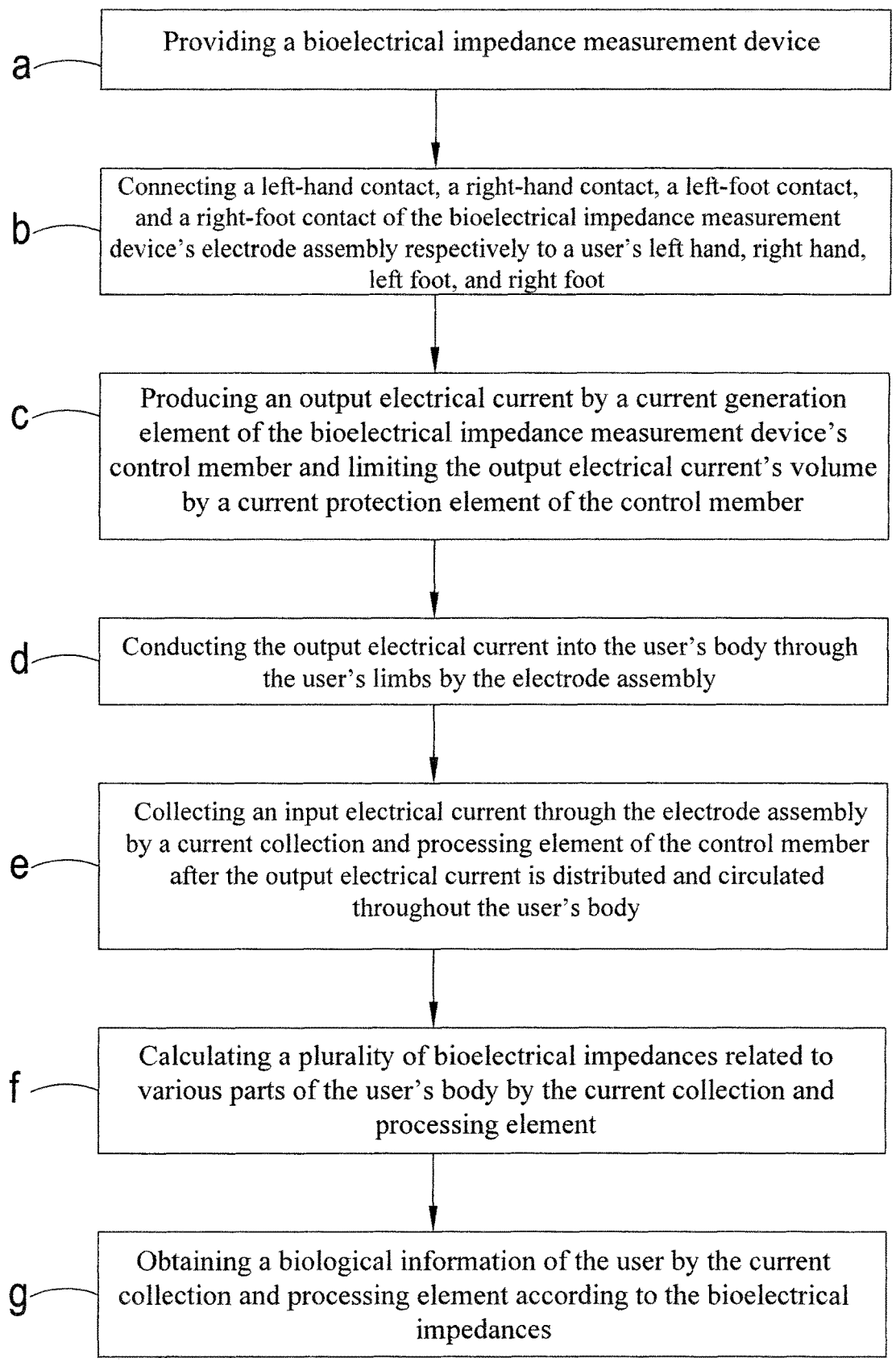
FIG. 2 is a flow diagram showing the steps of bioelectrical impedance measurement method according to a first embodiment of the present invention.
Figure 3:
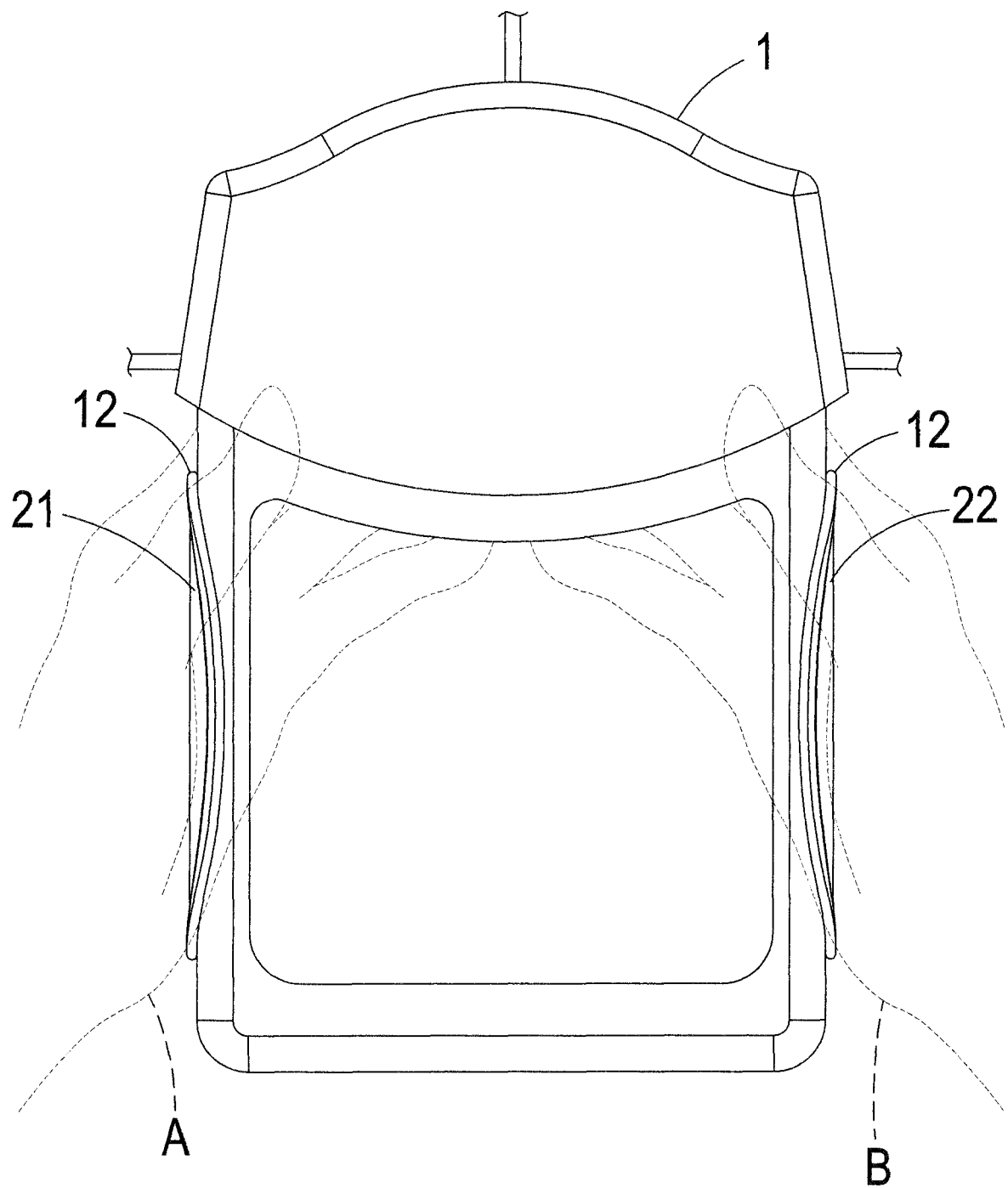
FIG. 3 shows how the bioelectrical impedance measurement device of FIG. 1 is held by a user's hands.
Figure 4:
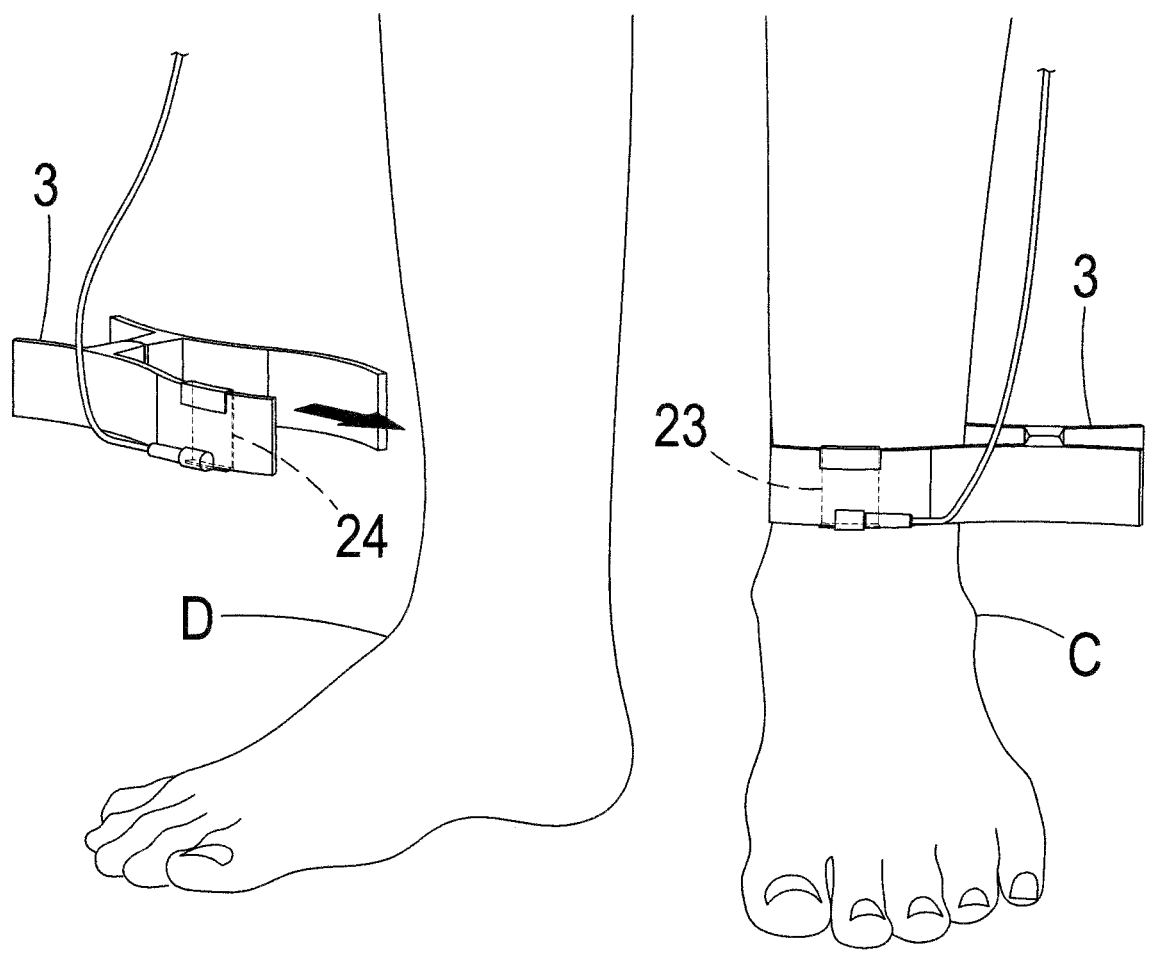
FIG. 4 shows how the bioelectrical impedance measurement device of FIG. 1 is clamped to a user's legs.
Figure 5:
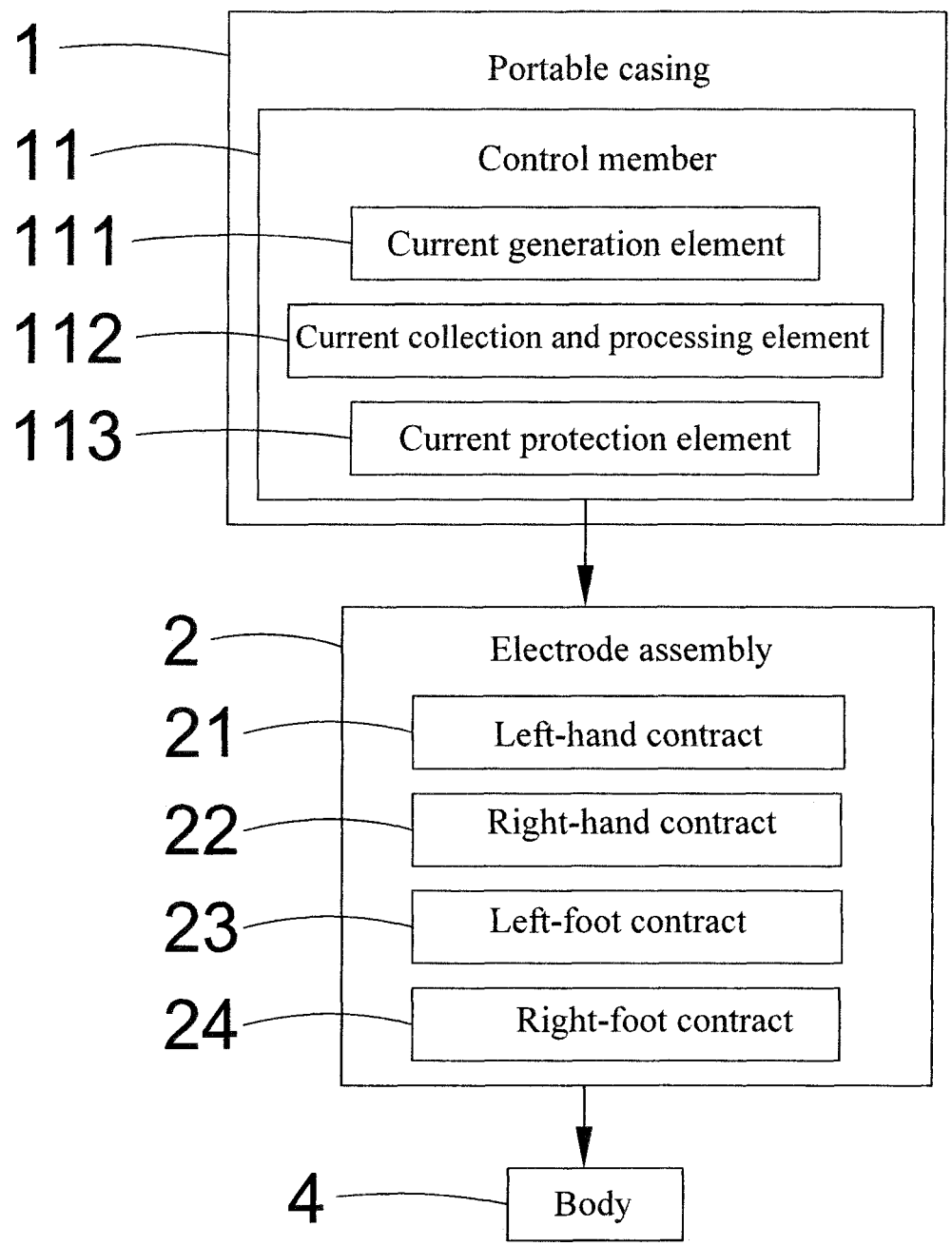
FIG. 5 is a block diagram showing how electrical current is introduced into a user's body through the bioelectrical impedance measurement device of FIG. 1.
Figure 6:
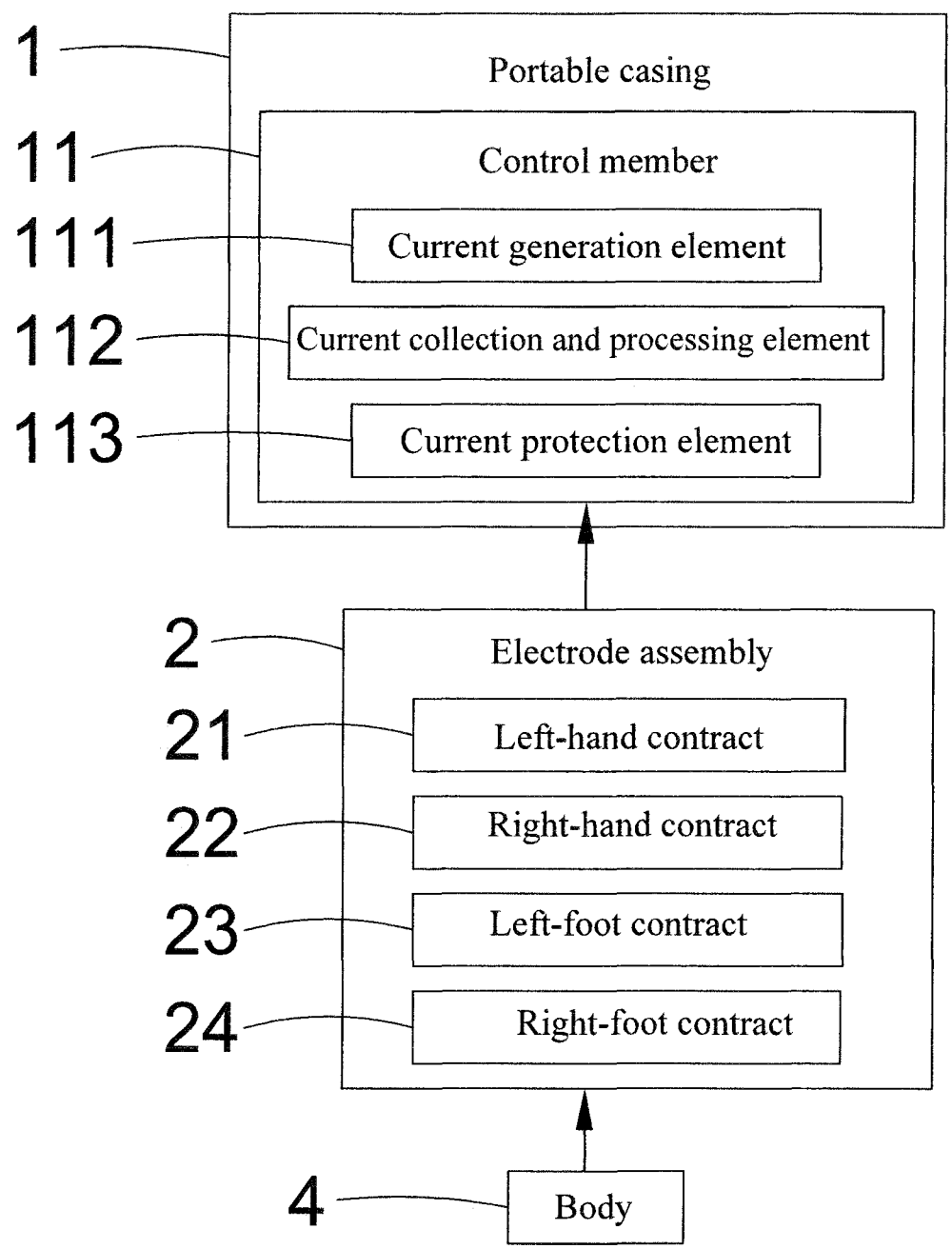
FIG. 6 is a block diagram showing how electrical current is collected from a user's body through the bioelectrical impedance measurement device of FIG. 1.
Figure 7:
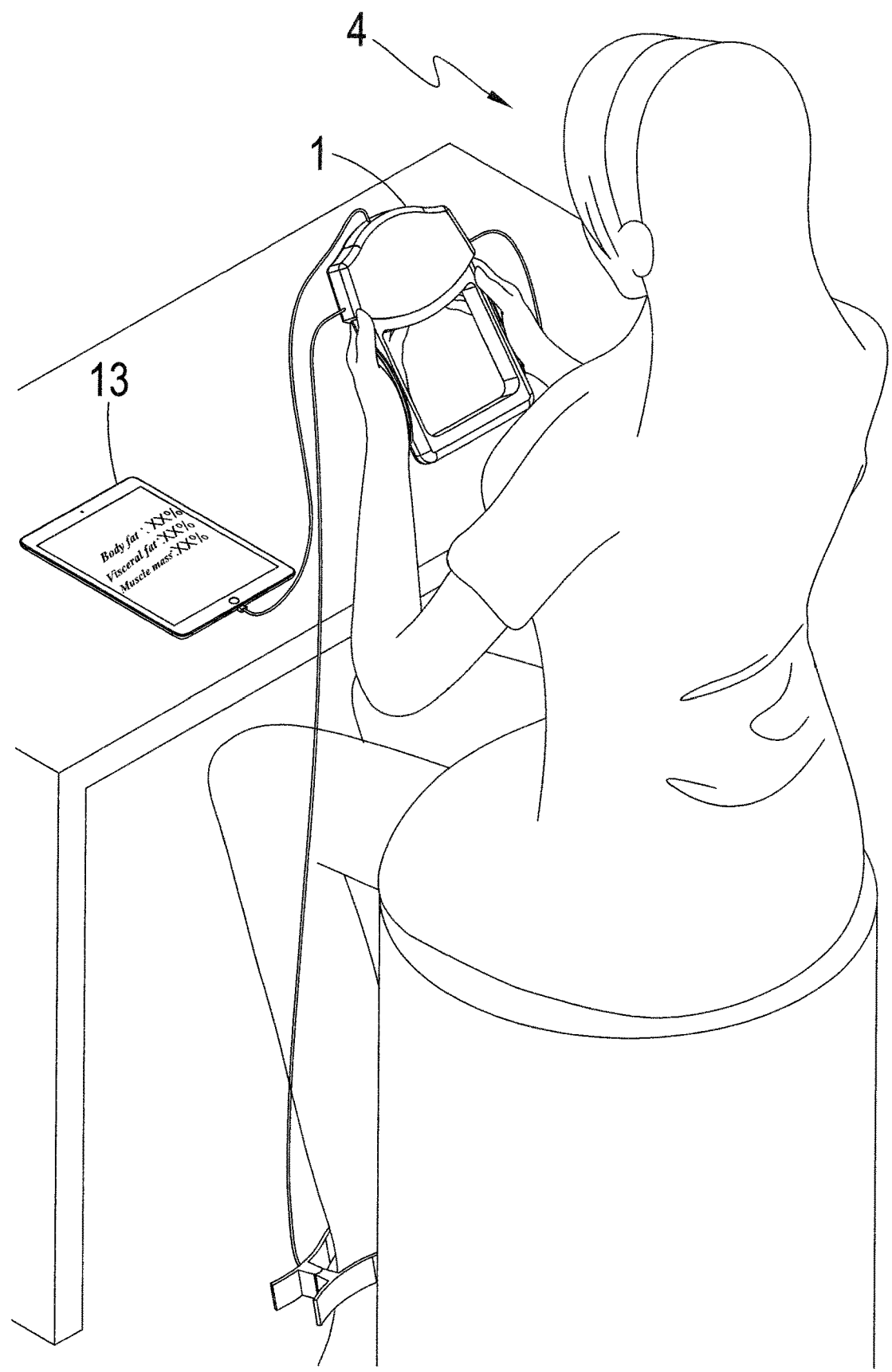
FIG. 7 provides an application scenario of the bioelectrical impedance measurement device of FIG. 1.

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

As shown in FIGS. 1 to 7, a bioelectrical impedance measurement device according an embodiment of the present invention includes the following components.

A portable casing 1 is provided.

A control member 11 is configured inside the portable casing 1. The control member 11 in the present embodiment is a circuit board. The control member 11 includes a current generation element 111, a current collection and processing element 112, and a current protection element 113.

A number of handle elements 12 are provided on the portable casing 1. In the present embodiment, the handle elements 12 are pads configured to two sides of the portable casing 1.

An electrode assembly 2 is connected to the portable casing 1. The electrode assembly 2 is electrically connected to the control member 11, and includes a left-hand contact 21 on a handle element 12, a right-hand contact 22 on another handle element 12, a left-foot contact 23 connected to the portable casing 1, and a right-foot contact 24 connected to the portable casing 1. In the present embodiment, the left-hand contact 21, right-hand contact 22, left-foot contact 23, and right-foot contact 24 are all electricity-conducting metallic pieces. The left-foot contact 23 and right-foot contact 24 are respectively configured on two foot fasteners 3. In the present embodiment, the foot fasteners 3 are clamps.

A display 13 is connected to the portable casing 1. In the present embodiment, the display 13 is an external flat panel connected to the portable casing 1.

According the above description, the bioelectrical impedance measurement device is convenient to carry and able to provide more accurate measurements, as will be elaborated as follows.

A bioelectrical impedance measurement method of the present invention include the following steps:

(a) providing a bioelectrical impedance measurement device as described above;

(b) connecting a left-hand contact, a right-hand contact, a left-foot contact, and a right-foot contact of the bioelectrical impedance measurement device's electrode assembly respectively to a user's left hand, right hand, left foot, and right foot;

(c) producing an output electrical current by a current generation element of the bioelectrical impedance measurement device's control member and limiting the output electrical current's volume by a current protection element of the control member;

(d) conducting the output electrical current into the user's body through his/her limbs by the electrode assembly;

(e) collecting an input electrical current through the electrode assembly by a current collection and processing element of the control member as the output electrical current is distributed and circulated throughout the user's body;

(f) calculating a number of bioelectrical impedances related to various parts of the user's body by the current collection and processing element; and (g) obtaining a biological information of the user by the current collection and processing element according to the bioelectrical impedances.

When a user holds the portable casing 1 with both hands, the left hand A and the right hand B firmly and fully contact the left-hand contact 21 and the right-hand contact 22, respectively. Then, by the foot fasteners 3, the left-foot contact 23 and right-foot contact 24 reliably and respectively contact the user body 4's left foot C and right foot D. As the left-hand contact 21, right-hand contact 22, left-foot contact 23, and right-foot contact 24 are reliably connected to the body 4's left hand A, right hand B, left foot C, and right foot D, the measurement accuracy is enhanced. The present embodiment also has the foot fasteners 3 clamping the body 4's ankles and, in contrast to the traditional approach's relying on the contact of soles, the present embodiment may achieve more reliable and complete contact. The ankles also have thinner skin thickness, providing more effective electrical conducting.

The control member 11 then has its current generation element 111 to produce an electrical current. The power source may be from an internal battery or from an external device, where the present invention is not limited as such. As the electrical current will enter user body, therefore, the current protection element 113 limits the electrical current under a threshold, preventing the electrical current from harming the user. After being confined by current protection element 113, the electrical current is distributed uniformly throughout the body 4 through the electrode assembly 2. An electrical current is then collected by the current collection and processing element 112 through the electrode assembly 2. As such, the biological impedances of the various parts of the body 4 are accurately measured. The current collection and processing element 112, based on the biological impedances, determines and displays the various biological information such as body fat percentage, visceral fat rate, muscle mass index, on the display 13. For example, the display 13 may show [Body fat: XX % Visceral fat: XX % Muscle mass: XX %]. The current collection and processing element 112 may further evaluate the health condition of the body 4, such as whether there is a chronic disease and congestive heart failure. The present invention is, therefore, convenient to carry and the measurement result is more accurate.

Figure 8:
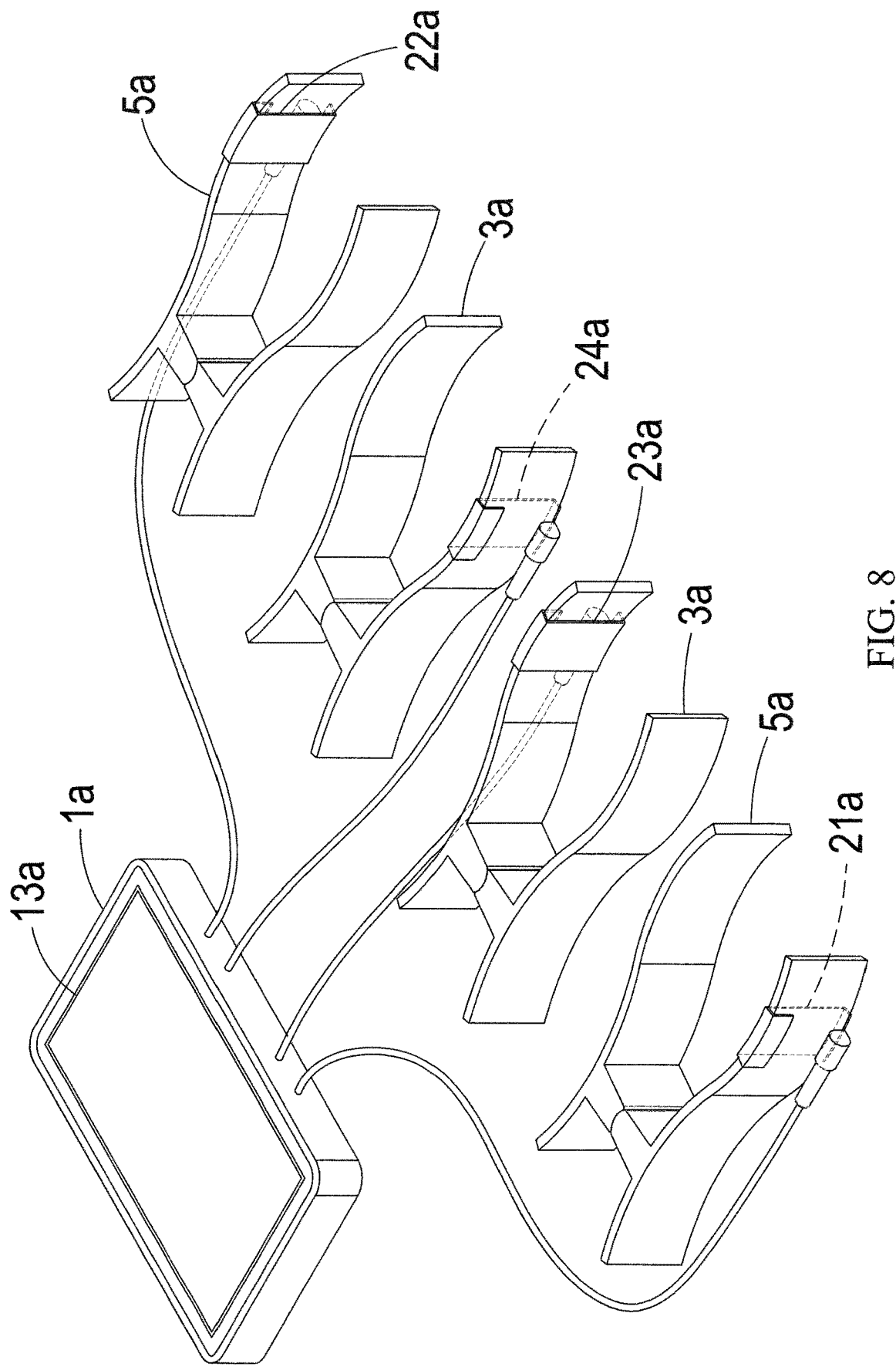
FIG. 8 is a perspective diagram showing a bioelectrical impedance measurement device according to a second embodiment of the present invention.
Figure 9:
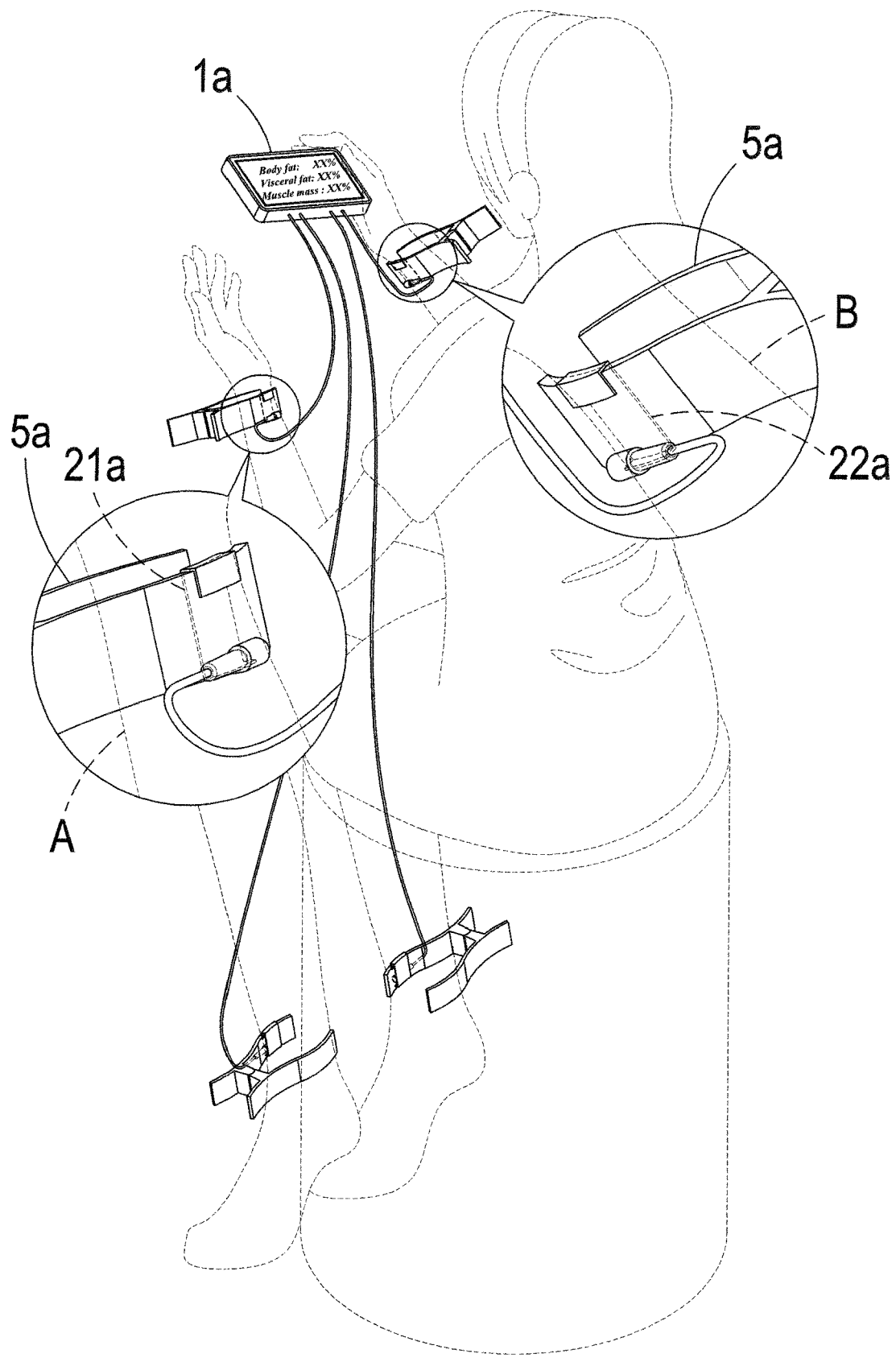
FIG. 9 shows how the bioelectrical impedance measurement device of FIG. 8 is connected a user's limbs.

As shown in FIGS. 8 and 9, a second embodiment of the present invention is similar to the previous embodiment except that, in the present embodiment, the handle elements 5a are also clamps similar to the foot fasteners 3a. The left-hand contact 21a and right-hand contact 22a are configured on the handle elements 5a, and the left-foot contact 23a and right-foot contact 24a are configured on the foot fasteners 3a. The display 13a is configured on the portable casing 1a. As such, a user may fix the left-hand contact 21a and right-hand contact 22a onto the left hand A and right hand B by the handle elements 5a for enhanced connection and convenience.

Figure 10:
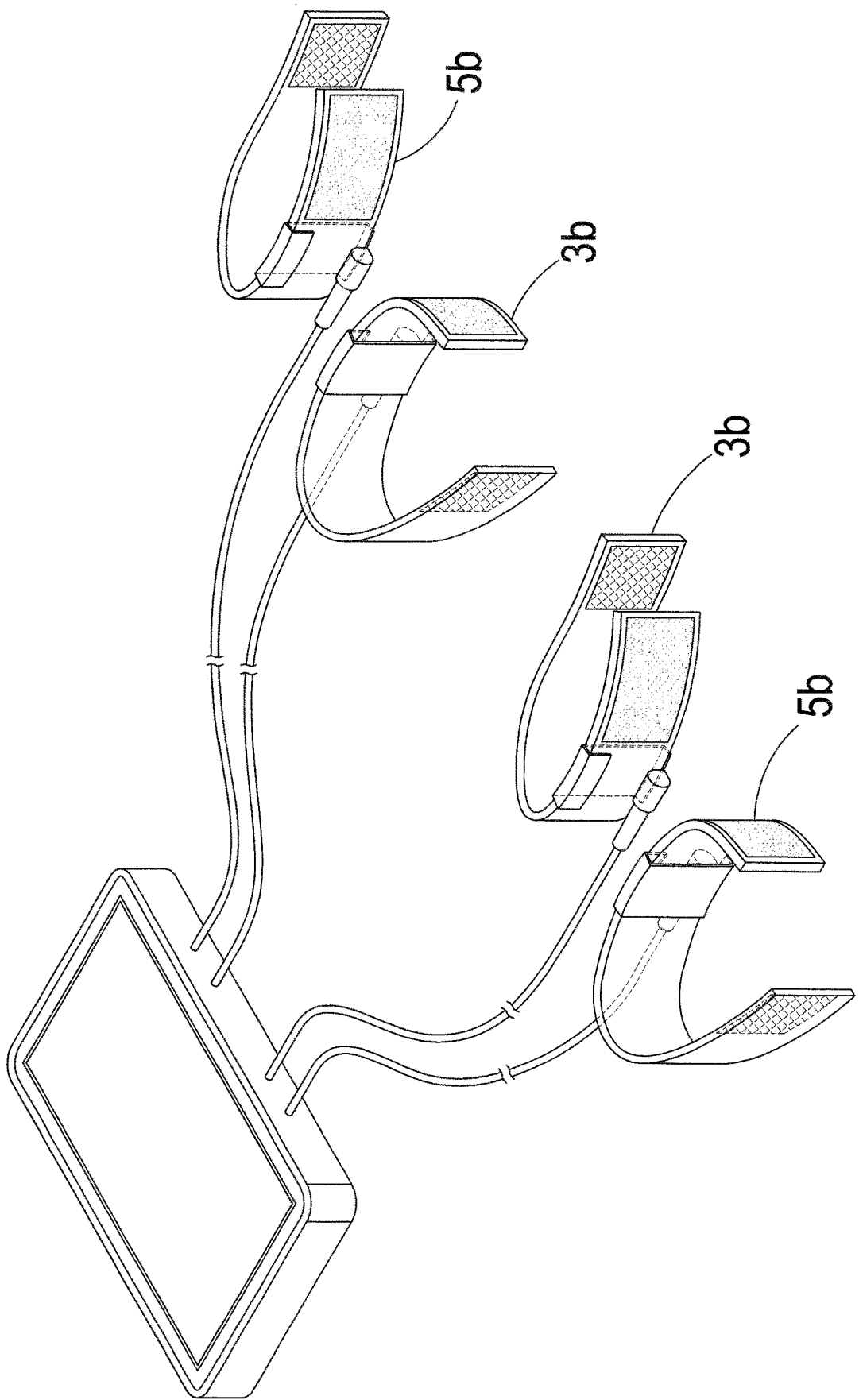
FIG. 10 is a perspective diagram showing a bioelectrical impedance measurement device according to a third embodiment of the present invention.

As shown in FIG. 10, a third embodiment of the present invention is similar to the previous embodiments except that, in the present embodiment, the handle elements 5b and foot fasteners 3b are bands with Velcro fasteners, demonstrating that the handle elements 5b and foot fasteners 3b may be embodied differently.

Figure 11:
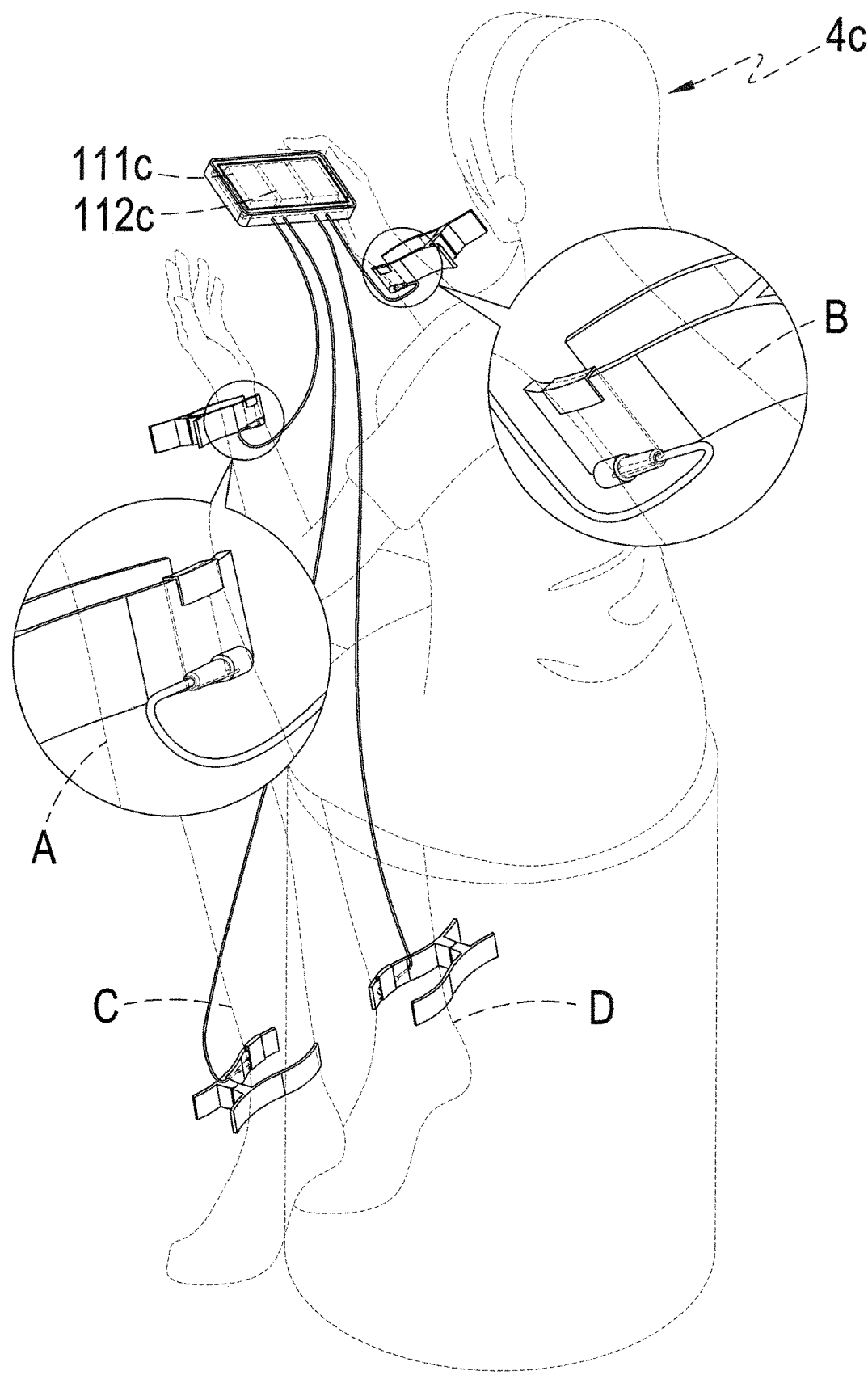
FIG. 11 shows how a bioelectrical impedance measurement method according a second embodiment of the present invention is applied to a user.
Figure 12:
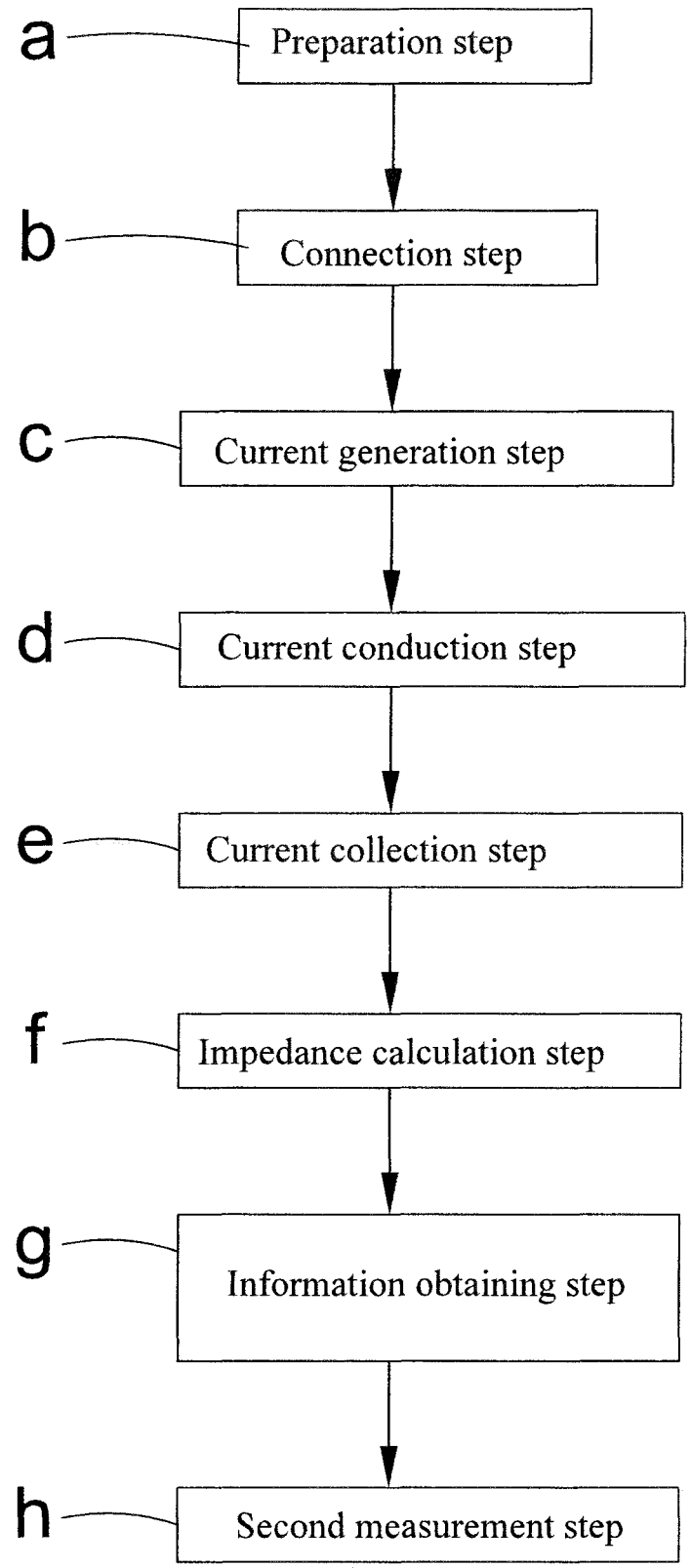
FIG. 12 is a flow diagram showing the major steps of a bioelectrical impedance measurement method according to a second embodiment of the present invention.

As shown in FIGS. 11 to 13, another embodiment of the bioelectrical impedance measurement method includes the following steps:

(a) A preparation step: providing a bioelectrical impedance measurement device as described above;

(b) A connection step: connecting a left-hand contact, a right-hand contact, a left-foot contact, and a right-foot contact of the bioelectrical impedance measurement device's electrode assembly respectively to a user's left hand, right hand, left foot, and right foot;

(c) A current generation step: producing a plurality of first output electrical currents by a current generation element of the bioelectrical impedance measurement device's control member and limiting the first output electrical currents' volumes by a current protection element of the control member;

(d) A current conduction step: conducting each first output electrical currents into the user's body through one of his/her limbs by the electrode assembly;

(e) A current collection step: collecting a plurality of input electrical currents through the electrode assembly by a current collection and processing element of the control member as the first output electrical currents are distributed and circulated throughout the user's body and exit the user body from a different limb other than a current's entering limb;

(f) An impedance calculation step: calculating a number of bioelectrical impedances related to various parts of the user's body by the current collection and processing element according to the respective first output electrical currents and first input electrical currents;

(g) An information obtaining step: obtaining a biological information of the user by the current collection and processing element according to the bioelectrical impedances; and (h) A second measurement step: producing a plurality of second output electrical currents having frequencies different from those of the first output electrical currents by the current generation element of the bioelectrical impedance measurement device's control member and repeating steps (d) to (g) for the second output electrical currents.

As described, in the present embodiment, the current generation element $111c$ produces a number of first output electrical currents, and each first output electrical current enters the body $4c$ through one of the limbs and a first input electrical current is collected from a different limb by the current collection and processing element $112c$. Then, a number of biological impedances corresponding to different entry and exit points are obtained, thereby enhancing the accuracy of derived biological information.

For example, a first electrical current is introduced through the left hand A and a first input electrical current is collected from the right foot D by the current collection and processing element $112c$. A biological impedance between the left hand A and the right foot D is thereby obtained. Then, another first output electrical current is introduced through the right hand B and another first input electrical current is collected from the left foot C so that another biological impedance between the right hand B and the left foot C is determined. This process then may be repeated between different pairs of limbs. In the present embodiment, the biological impedance between the left hand A and the right foot D is defined as AD impedance, the one between the left hand A and the right hand B as AB impedance, the one between the left hand A and the left foot C as AC impedance, the one between the right hand B and the left foot C as BC impedance, the one between the right hand B and the right foot D as BD impedance, and the one between the left foot C and the right foot D as CD impedance. These biological impedances are then compared against each other so that different biological information may be derived as these impedances cover various organs and muscles. For example, if AD impedance is greater than BC impedance, it is possibly due to that left hand A has a greater muscle mass than that of right hand B. Therefore, by comparing pairs of these biological impedances, the various portions of muscle and fat of the body or organs may be derived and one or more biological information may be determined with greater accuracy.

After a first round of measurement, in the present embodiment, the current generation element $111c$ produces a number of second output electrical currents whose frequencies are different from the first output electrical currents. Then, a same process is repeated for the second output electrical currents to obtain another set of AD impedance, AB impedance, AC impedance, BC impedance, BD impedance, and CD impedance. As human body $4c$ has a large amount of water, different impedances are detected by electrical currents of different frequencies. For example, AD impedance detected under output electrical currents of frequencies 1k, 5k, 50k, 250k, and 500k is respectively Z1, Z2, Z3, Z4, and Z5, AB impedance is respectively Y1 to Y5, AC impedance is respectively X1 to X5, BC impedance is respectively W1 to W5, BD impedance is respectively V1 to V5, and CD impedance is respectively U1 to U5. Then, by the differences between these impedances, the portion of water inside the body $4c$ may be estimated and this information is used to fine-tune the derived biological information for even greater accuracy.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the claims of the present invention.

We claim:

1. A bioelectrical impedance measurement device, comprising:

a portable casing;

a control member inside the portable casing, where the control member comprises a current generation element, which comprises a power supply;

an electrode assembly connected to the portable casing and electrically connected to the control member, where the electrode assembly comprises a left-hand contact, a right-hand contact, a left-foot contact, and a right-foot contact;

wherein the power supply of the current generation element supplies an output electrical current to a user's body through user's limbs by the electrode assembly so that the output electrical current flows through the user's body and an input electrical current is induced in the user's body to be collected by the control member through the electrode assembly; and at least a biological impedance is determined by the control member according to the input electrical current collected from the user's body; and wherein the portable casing comprises two opposite sides to each of which a handle element in the form of a pad is mounted, the pads of the handle elements being adapted to be gripped by the user's left and right hands for hand-holding the portable casing, and wherein each of the left-hand contact and the right-hand contact comprises an electricity-conducting metallic piece arranged on a corresponding one of the pads of the handle elements to contact the user's left and right hands, in order to electrically connect the user's left and right hands to the control member by means of the left-hand contact and the right-hand contact of the electrode assembly.

2. The bioelectrical impedance measurement device according to claim 1, wherein each of the left-foot contact and the right-foot contact is configured on a foot fastener for attaching the left-foot contact and the right-foot contact to a user's left foot and right foot.

3. The bioelectrical impedance measurement device according to claim 1, further comprising a display connected to the portable casing and electrically connected to the control member.

4. A bioelectrical impedance measurement method, comprising:

(a) providing a bioelectrical impedance measurement device that comprises a portable casing, an electrode assembly, and a control member, wherein the electrode assembly is connected to the portable casing and is electrically connected to the control member;

(b) connecting a left-hand contact, a right-hand contact, a left-foot contact, and a right-foot contact of the electrode assembly respectively to a user's left hand, right hand, left foot, and right foot;

(c) producing and supplying an output electrical current from the control member and limiting a current volume of the output electrical current to a predetermined level;

(d) conducting the output electrical current into the user's body through the user's left hand, right hand, left foot, and right foot by the electrode assembly such that the output electrical current is distributed and circulated throughout the user's body and produces an input electrical current;

(e) collecting the input electrical current from the user's body through the electrode assembly by the control member;

(f) calculating a plurality of bioelectrical impedances related to various parts of the user's body by the control member; and (g) obtaining biological information of the user's body by the control member according to the bioelectrical impedances, wherein the portable casing comprises two opposite sides to each of which a handle element in the form of a pad is mounted, the pads of the handle elements being adapted to be gripped by the user's left and right hands for hand-holding the portable casing, and wherein each of the left-hand contact and the right-hand contact comprises an electricity-conducting metallic piece arranged on a corresponding one of the pads of the handle elements to contact the user's left and right hands, in order to electrically connect the user's left and right hands to the control member by means of the left-hand contact and the right-hand contact of the electrode assembly.

5. The bioelectrical impedance measurement method according to claim 4, wherein each of the left-foot contact and the right-foot contact is configured on a foot fastener for attaching the left-foot contact and the right-foot contact to the user's left foot and right foot.

6. A bioelectrical impedance measurement method, comprising:

(a) providing a bioelectrical impedance measurement device that comprises a portable casing, an electrode assembly, and a control member, wherein the electrode assembly is connected to the portable casing and is electrically connected to the control member;

(b) connecting a left-hand contact, a right-hand contact, a left-foot contact, and a right-foot contact of the electrode assembly respectively to a user's left hand, right hand, left foot, and right foot;

(c) producing and supplying a plurality of first output electrical currents having predetermined frequencies from the control member and limiting current volumes of the first output electrical currents to predetermined levels;

(d) conducting each of the first output electrical currents into the user's body through one of the user's left hand, right hand, left foot, and right foot by the electrode assembly such that the output electrical currents are distributed and circulated throughout the user's body and produce a plurality of input electrical currents;

(e) collecting the plurality of input electrical currents from the user's body through the electrode assembly by the control member from a different one of the user's left hand, right hand, left foot, and right foot that is other than the one of the user's left hand, right hand, left foot, and right foot through which the first output electrical currents are conducted into the user's body;

(f) calculating a plurality of bioelectrical impedances related to various parts of the user's body by the control member according to the respective first output electrical currents and first input electrical currents;

(g) obtaining biological information of the user's body by the control member according to the bioelectrical impedances; and (h) producing and supplying a plurality of second output electrical currents having frequencies different from the predetermined frequencies of the first output electrical currents from the control member and repeating steps (d) to (g) for the second output electrical currents, wherein the portable casing comprises two opposite sides to each of which a handle element in the form of a pad is mounted, the pads of the handle elements being adapted to be gripped by the user's left and right hands for hand-holding the portable casing, and wherein each of the left-hand contact and the right-hand contact comprises an electricity-conducting metallic piece arranged on a corresponding one of the pads of the handle elements to contact the user's left and right hands, in order to electrically connect the user's left and right hands to the control member by means of the left-hand contact and the right-hand contact of the electrode assembly.

7. The bioelectrical impedance measurement method according to claim 6, wherein each of the left-foot contact and the right-foot contact is configured on a foot fastener for attaching the left-foot contact and the right-foot contact to the user's left foot and right foot.

* * * * *